United States Patent
Seo (10) Patent No.: US 10,251,266 B2
(45) Date of Patent: Apr. 2, 2019

(54) WEARABLE FLEXIBLE PRINTED CIRCUIT BOARD AND METHOD OF MANUFACTURING THE SAME

(71) Applicant: AMOGREENTECH CO., LTD., Gimpo-si (KR)

(72) Inventor: In Yong Seo, Seoul (KR)

(73) Assignee: AMOGREENTECH CO., LTD., Gimpo-si (KR)

( * ) Notice: Subject to any disclaimer, the term of this patent is extended or adjusted under 35 U.S.C. 154(b) by 0 days.

(21) Appl. No.: 15/896,549

(22) Filed: Feb. 14, 2018

(65) Prior Publication Data
US 2018/0192514 A1    Jul. 5, 2018

Related U.S. Application Data

(63) Continuation-in-part of application No. PCT/KR2016/009233, filed on Aug. 22, 2016.

(30) Foreign Application Priority Data

Aug. 21, 2015  (KR) .................. 10-2015-0117901

(51) Int. Cl.
*H05K 1/03* (2006.01)
*B32B 5/06* (2006.01)
(Continued)

(52) U.S. Cl.
CPC ............. *H05K 1/038* (2013.01); *A41D 1/002* (2013.01); *A61B 5/6804* (2013.01); *B32B 5/06* (2013.01);
(Continued)

(58) Field of Classification Search
CPC .............................. H05K 1/038; H05K 1/189
(Continued)

(56) References Cited

U.S. PATENT DOCUMENTS

| 5,763,058 A | 6/1998 | Isen et al. | |
|---|---|---|---|
| 2004/0098923 A1* | 5/2004 | Hood | B24D 3/348 |
| | | | 51/296 |

(Continued)

FOREIGN PATENT DOCUMENTS

| JP | 2015088536 | 5/2015 |
|---|---|---|
| JP | 2015088537 | 5/2015 |

(Continued)

OTHER PUBLICATIONS

International Search Report—PCT/KR2016/009233 dated Nov. 18, 2016.

*Primary Examiner* — Sherman Ng
(74) *Attorney, Agent, or Firm* — Cantor Colburn LLP (57) ABSTRACT

Provided is a wearable flexible printed circuit board, in which a conductive circuit pattern is formed on a fiber web formed by accumulating fibers, and thus a base substrate has flexibility, resilience, waterproofness and air-permeability so as to be applied to future-oriented devices, a manufacturing method thereof, and a wearable smart device using the same. The wearable flexible printed circuit board includes: a base substrate made of a fiber web that is formed by accumulating spun fibers made of a fiber-forming polymer material and having a diameter of 3 μm or less; and a conductive circuit pattern formed on the base substrate.

18 Claims, 9 Drawing Sheets
(1 of 9 Drawing Sheet(s) Filed in Color)

(51) Int. Cl.
| | |
|---|---|
| *A41D 1/00* | (2018.01) |
| *A61B 5/00* | (2006.01) |
| *H05B 3/36* | (2006.01) |
| *H05K 1/02* | (2006.01) |
| *H05K 3/00* | (2006.01) |
| *H05K 3/12* | (2006.01) |
| *H05K 1/16* | (2006.01) |
| *H01Q 1/38* | (2006.01) |
| *H05K 1/18* | (2006.01) |
| *H01Q 1/22* | (2006.01) |
| *H01Q 7/00* | (2006.01) |

(52) U.S. Cl.
CPC .............. *H05B 3/36* (2013.01); *H05K 1/0212* (2013.01); *H05K 1/0281* (2013.01); *H05K 1/165* (2013.01); *H05K 1/167* (2013.01); *H05K 3/0011* (2013.01); *H05K 3/1283* (2013.01); *A61B 2562/164* (2013.01); *A61B 2562/166* (2013.01); *H01Q 1/2225* (2013.01); *H01Q 1/38* (2013.01); *H01Q 7/00* (2013.01); *H05K 1/189* (2013.01); *H05K 2201/0116* (2013.01); *H05K 2201/10098* (2013.01); *H05K 2201/10151* (2013.01)

(58) Field of Classification Search
USPC .......................................................... 174/254
See application file for complete search history.

(56) References Cited

U.S. PATENT DOCUMENTS

| | | | |
|---|---|---|---|
| 2005/0195118 A1* | 9/2005 | Ito ...................... | A61B 1/00016 343/718 |
| 2009/0291604 A1* | 11/2009 | Park ................... | A41D 31/0038 442/164 |
| 2010/0206614 A1* | 8/2010 | Park ...................... | H01H 13/88 174/126.1 |
| 2013/0078882 A1* | 3/2013 | Yoo ...................... | D01D 5/0038 442/335 |
| 2014/0335459 A1* | 11/2014 | Im .............................. | G03F 7/20 430/324 |
| 2015/0005728 A1* | 1/2015 | Sheehan .............. | A61F 13/5323 604/372 |
| 2015/0235731 A1* | 8/2015 | Park ........................ | H01B 1/22 252/514 |
| 2016/0195488 A1* | 7/2016 | Ensor ................. | G01N 33/0047 422/69 |
| 2017/0005504 A1* | 1/2017 | Rho ....................... | H02J 7/025 |

FOREIGN PATENT DOCUMENTS

| | | |
|---|---|---|
| KR | 101139970 | 4/2012 |
| KR | 20130129104 | 11/2013 |
| KR | 20130129105 | 11/2013 |

* cited by examiner

WEARABLE FLEXIBLE PRINTED CIRCUIT BOARD AND METHOD OF MANUFACTURING THE SAME

TECHNICAL FIELD

The present invention relates to a wearable flexible printed circuit board, and more particularly, to a wearable flexible printed circuit board, in which a conductive circuit pattern is formed on a fiber web formed by accumulating fibers, and thus a base substrate has flexibility, resilience, waterproofness and air-permeability so as to be applied to future-oriented devices, a manufacturing method thereof, and a wearable smart device using the same.

BACKGROUND ART

In general, printed circuit boards (PCBs) are components that become the basis for various electrical and electronic products.

In other words, PCBs are essential for household electrical appliances. In recent years, miniaturized, high-density, and high-performance printed circuit boards have been used for semiconductor modules, semiconductor inspection devices, automobiles, as well as defense industry advanced weapon such as missile warheads, fighters and satellites. The use of PCBs is gradually expanding.

A conventional printed circuit board is classified into a rigid printed circuit board in which a copper foil is adhered to a core material to which a reinforcing material such as glass fibers is added to an epoxy resin, a flexible printed circuit board (FPCB) in which a copper foil is adhered to a Polyimide substrate, and a rigid-flexible printed circuit board (RF PCB) that combines the merits of a rigid printed circuit board with a flexible printed circuit board. The respective PCBs are used in accordance with their characteristics.

Meanwhile, future type devices to be developed and utilized in the future are expected to be structurally and conceptually different from existing devices. In particular, recently, glasses, clothing, and the like, which are worn on the human body for convenient human life, are beginning to be developed by being built in together with electronic components.

Development of a wearable printed circuit board in the course of such changes may facilitate the development of future type devices such as smart clothes, and research and development of the technology will be necessary.

Korean Patent Registration No. 10-1139970 (Patent Document 1) discloses a method of manufacturing a flexible printed circuit board, the method comprising: a first step of forming a circuit pattern on a seed layer formed on a flexible insulating substrate; a second step of applying a first photosensitive material on the circuit pattern; a third step of exposing and developing the first photosensitive material to form a protective pattern on the circuit pattern; a fourth step of etching the seed layer; and a fifth step of peeling off the protective pattern, wherein the first photosensitive material is a liquid or film type photosensitive material.

Patent Document 1 discloses implementing a flexible printed circuit board. However, since the base member is a flexible insulating substrate such as a polyimide film, there is no restoring characteristic of being folded, crumpled and then spread again, and there is no air-permeability. As a result, such a flexible printed circuit board is not applicable to smart clothes and the like which require wearability.

DISCLOSURE

Technical Problem

The present invention has been made in view of the above-mentioned problems, and it is an object of the present invention to provide a wearable flexible printed circuit board, in which a conductive circuit pattern is formed on a fiber web formed by accumulating fibers, to thus improve a warping characteristic and a restoring characteristic capable of being restored to an original flat state from a folded or wrinkled state, a method of manufacturing the same, and a wearable smart device using the wearable flexible printed circuit board.

Another object of the present invention is to provide a wearable flexible printed circuit board and a method of manufacturing the wearable flexible printed circuit board which satisfy the waterproof property and the breathability characteristic required for wearable smart clothing by applying a fiber web having a plurality of pores formed by accumulating nano-size fibers as a base substrate for the wearable flexible printed circuit board.

Technical Solution

In order to achieve the above-mentioned object, there is provided a wearable flexible printed circuit board according to an aspect of the present invention comprising: a base substrate made of a fiber web that is formed by accumulating spun fibers made of a fiber-forming polymer material and having a diameter of 3 μm or less; and a conductive circuit pattern formed on the base substrate.

In the wearable flexible printed circuit board according to an embodiment of the present invention, the fiber web may have a plurality of pores. The porosity of the fiber web may be in a range of 40% to 80%.

In the wearable flexible printed circuit board according to an embodiment of the present invention, the circuit pattern may be formed by filling a conductive paste into the fibers and the pores of the fiber web.

In the wearable flexible printed circuit board according to an embodiment of the present invention, the circuit pattern may be formed on the fibers of the fiber web.

In the wearable flexible printed circuit board according to an embodiment of the present invention, the fiber web may be formed by accumulating fibers obtained by electrospinning a spinning solution containing a mixture of a polymer material and a solvent.

In addition, the base substrate may have a thickness of 20 μm to 100 μm and when the circuit patterns are formed on the upper and lower sides of the base substrate, respectively, the circuit patterns formed on the upper and lower sides may not be electrically conducted with each other.

Furthermore, the thickness of the base substrate may be in a range of 5 μm to 20 μm, and the circuit patterns formed on the base substrate may be vertically electrically conducted.

In the wearable flexible printed circuit board according to an embodiment of the present invention, the circuit pattern may be formed by a conductive paste printed on the fiber web. In this case, the conductive paste may be an Ag paste or a Cu paste.

In addition, the base substrate may further include: a strength reinforcing support; and the fiber web laminated on one side or both sides of the support.

In the wearable flexible printed circuit board according to an embodiment of the present invention, the fibers may be corrugated fibers or straight fibers.

In the wearable flexible printed circuit board according to an embodiment of the present invention, the fiber web may be a three-layer fiber web structure composed of an upper layer, an intermediate layer and a lower layer, and the intermediate layer of the fiber web is thinner than the upper or lower layer in diameter, or a non-porous web.

In the wearable flexible printed circuit board according to an embodiment of the present invention, the fiber diameter of the intermediate layer is in a range of 400 nm to 500 nm, and the fiber diameters of the upper and lower layers may be more than 500 nm.

Further, the base substrate may include the fiber web in a non-porous form.

For achieving the object of the present invention, there is provided a wearable smart device including: a wearable flexible printed circuit board on which a conductive circuit pattern is formed on a porous base substrate having flexible, air-permeable and waterproof characteristics; and at least one electronic component mounted on the wearable flexible printed circuit board.

In the wearable smart device according to an embodiment of the present invention, the electronic component includes: a sensor unit including at least one of a biosensor for detecting a user's physical condition and an environmental sensor for sensing a surrounding environment; a short range communication module used for short range wireless communication; an antenna pattern used for wireless communication; and a control unit for performing a signal processing function.

In the wearable smart device according to an embodiment of the present invention, the electronic component may further include a heater pattern for generating heat according to an external environment.

In this case, the antenna pattern and the heater pattern may be formed directly on the printed circuit board by using a conductive paste.

In the wearable smart device according to an embodiment of the present invention, the electronic component may be one of a biosensor and a heater pattern for detecting a user's physical condition.

In the wearable smart device according to an embodiment of the present invention, the wearable smart device may be embedded between a cloth for lining and a cloth for outsheath or laminated inside the cloth for lining.

For achieving the object of the present invention, there is provided a method of manufacturing a wearable flexible printed circuit board including the steps of: forming a base substrate composed of a fiber web having a plurality of pores by accumulating fibers obtained by electrospinning a spinning solution containing a mixture of a polymer and a solvent; printing a conductive paste on the base substrate to form a circuit pattern; and curing the printed conductive paste.

In the method of manufacturing a wearable flexible printed circuit board according to an embodiment of the present invention, in the step of forming circuit patterns by printing a conductive paste on the fiber web, the circuit patterns may be formed on the fibers and pores of the fiber web, or on the fibers of the fiber web.

In the method of manufacturing a wearable flexible printed circuit board according to an embodiment of the present invention, in the step of forming the base substrate, the base substrate may be made of the fiber web formed by accumulating the corrugated fibers obtained by electrospinning the spinning solution in a humidity environment of 60% to 80%.

In the method of manufacturing a wearable flexible printed circuit board according to an embodiment of the present invention, in the step of forming the base substrate, the base substrate may be made of the fiber web formed by accumulating the straight fibers obtained by electrospinning the spinning solution in a humidity environment of 60% to 80%.

Advantageous Effects

According to some embodiments of the present invention, a printed circuit board is formed by forming a conductive circuit pattern on a fiber web formed by accumulating fibers as a base substrate, to thereby have an excellent warping characteristic in comparison with a polyimide film used in general flexible printed circuit boards and a restoration characteristic (a characteristic capable of returning to an original flat state although being folded or wrinkled) that does not exist in the polyimide film.

According to some embodiments of the present invention, there is an advantage that a base substrate of a printed circuit board may be made of a web-shaped sheet formed by accumulating fibers obtained by electrospinning a spinning solution, to thereby realize an ultra-thin printed circuit board.

According to some embodiments of the present invention, when a fiber web having a plurality of pores formed by accumulating nano-sized fibers is applied as a base substrate of a printed circuit board, the printed circuit board may have waterproof property and air-permeability, to thereby manufacture a wearable printed circuit board that may be worn by a user. In addition, when a printed circuit board having waterproofness, air-permeability and flexibility is embedded between a cloth lining and a cloth outsheath, there is an advantage that the printed circuit board may be applied to various future type devices such as smart clothes.

In some embodiments of the present invention, various types of sensors, signal processing devices, antennas and the like may be directly mounted on a printed circuit board having waterproofness, air-permeability and flexibility, to thus be applied variously to healthcare clothes that continuously monitors a wearer's heart rate, breathing, etc., entertainment clothes in which a keypad is inserted into small IT devices to then be operated, environmentally sensitive clothes that respond to changes in the external environment such as sound or light, and special clothes for military use.

According to some embodiments of the present invention, a fibrous web formed by accumulating corrugated fibers is applied to a flexible printed circuit board, thereby maximizing flexibility of the flexible printed circuit board.

BRIEF DESCRIPTION OF THE DRAWINGS

The patent application file contains at least one drawing executed in color. Copies of this patent or patent application publication with color drawing(s) will be provided by the Office upon request and payment of the necessary fee.

BEST MODE

Hereinafter, embodiments of the present disclosure will be described in detail with reference to the accompanying drawings.

Figure 1:
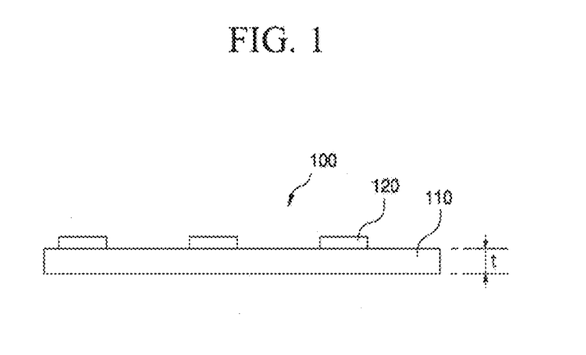
FIG. 1 is a conceptual cross-sectional view for explaining a wearable flexible printed circuit board according to an embodiment of the present invention.

Referring to FIG. 1, a wearable flexible printed circuit board (PCB) 100 according to an embodiment of the present invention includes: a fiber-web 110 obtained by accumulating fibers obtained by electrospinning a spinning solution containing a mixture of a fiber-forming polymer material and a solvent and used as a base substrate; and a conductive circuit pattern 120 formed on the fiber web 110.

Since the fiber web 110 is made by accumulating polymer fibers, the fiber web 110 has an excellent warping characteristic in comparison with a polyimide film used in general flexible printed circuit boards and a restoration characteristic capable of returning to an original flat state although being folded or wrinkled and that does not exist in the polyimide film.

Figure 2:
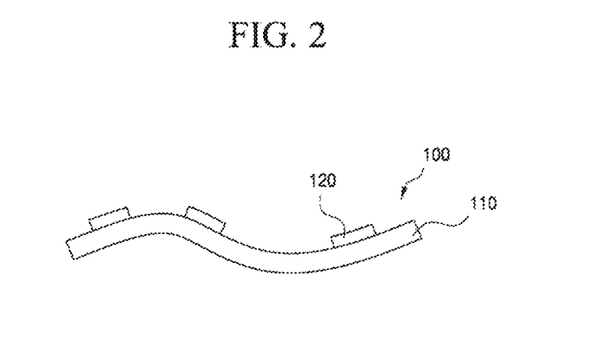
FIG. 2 is a conceptual cross-sectional view for explaining the flexibility of a wearable flexible printed circuit board according to an embodiment of the present invention.
Figure 8:
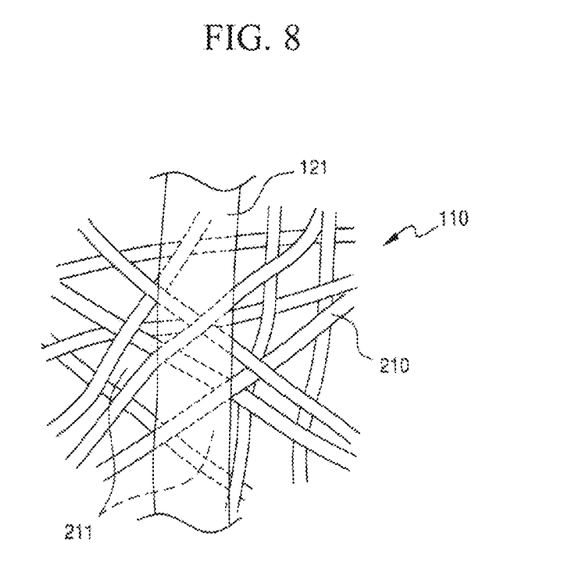
FIG. 8 is a schematic view for explaining a state in which a circuit pattern is formed on a fiber web according to an embodiment of the present invention.
Figure 9:
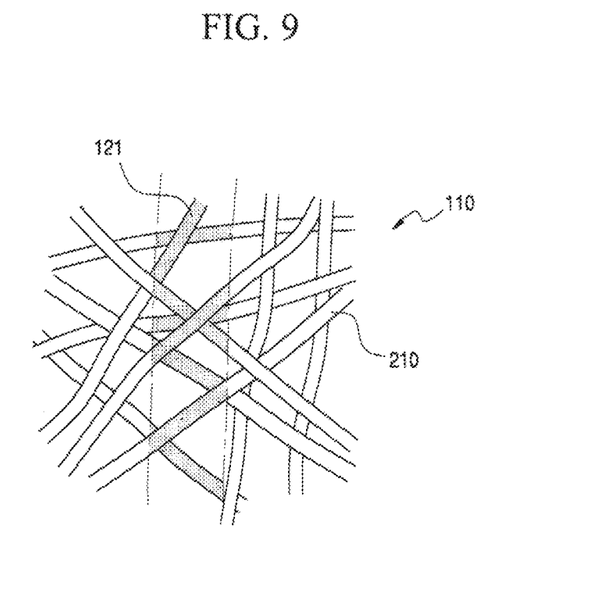
FIG. 9 is a schematic diagram for explaining formation of a circuit pattern in a fiber web in different states according to an embodiment of the present invention.

That is, since the wearable flexible printed circuit board 100 according to an embodiment of the present invention has the conductive circuit patterns 120 or 121 formed on the surfaces of the fibers 210 constituting the fiber web 110 as shown in FIGS. 2, 8 and 9, the circuit pattern 120 formed on the fibers is bent when the fiber web 110 is bent as shown in FIG. 2 by the excellent flexibility of each fiber 210 (see FIG. 9) and the portion where the conductive circuit patterns 120 or 121 are not formed. Accordingly, the wearable flexible printed circuit board 100 has flexibility. In addition, since the printed circuit board 100 according to an embodiment of the present invention is formed by randomly accumulating a plurality of fibers 210, the printed circuit board 100 may have the minimum restoration characteristic required for the wearable flexible printed circuit board 100 after being folded or crumpled.

In addition, the fiber web 110 is a sheet of a web structure formed by accumulating nanofibers obtained by electrospinning a spinning solution containing a mixture of a fiber-forming polymer material and a solvent. Therefore, the thickness t of the fiber web 110 may be minimized, that is, formed in a thin type at maximum. As a result, the fiber web may be used as a base substrate of a wearable flexible printed circuit board, and may be applied to smart clothing that enables realization of healthcare clothes, entertainment clothes, environmentally sensitive clothes, and military special purpose clothes.

In this case, the fiber web 110 may be obtained by electrospinning the spinning solution to have a fiber diameter of, for example, in the range of 400 nm to 3 μm, and the thickness of the fiber web 110 preferably in a range of 0.005 mm to 5 mm, more preferably, in a range of 5 μm to 100 μm.

The fiber web 110 may be formed in a porous film state or in a non-porous state having a plurality of fine pores 211 as shown in FIGS. 8 and 9 by falling and accumulating fibers obtained by electrospinning.

Here, when the fiber web 110 has a plurality of pores 211, the wearable flexible printed circuit board may be provided with air-permeability. Therefore, the wearable flexible printed circuit board has an optimal function and structure so as to be applied as a printed circuit board necessary for constructing a circuit by interconnecting a wearable garment to be worn on a human body and various parts of an electronic apparatus.

That is, sweat is generated in the human body, to control the body temperature according to the external environment, and the sweat is evaporated and discharged to the outside in a water vapor state. The water vapor vaporized from sweat passes through the wearable flexible printed circuit board according to an embodiment of the present invention having air-permeability, to then be discharged to the outside. Accordingly, the wearable flexible printed circuit board according to the embodiment of the present invention becomes a printed circuit board having flexible, air-permeable, and waterproof functions required of a wearable printed circuit board in comparison with a conventional flexible printed circuit board having no air-permeability.

Particularly, since the fiber diameters of the fibers of the fiber web 110 may be implemented in a nano-size of 3 μm or less, the pore size of the fiber web 110 becomes small.

Figure 3:
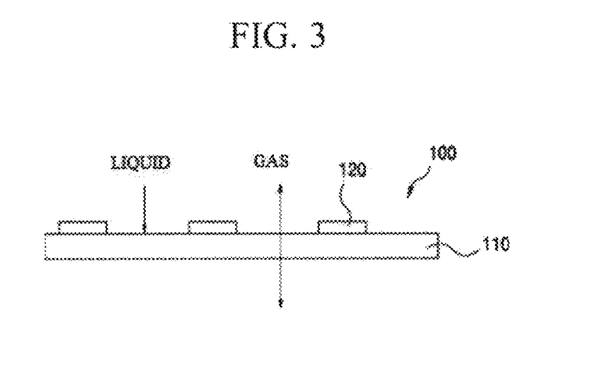
FIG. 3 is a conceptual cross-sectional view for explaining the air-permeability and waterproofness of a wearable flexible printed circuit board according to an embodiment of the present invention.

Accordingly, as shown in FIG. 3, the fiber web 110 may have waterproofness and air-permeability in which gas passes through the fiber web 110 but the liquid cannot pass through the fiber web 110. Therefore, the wearable flexible printed circuit board according to the embodiment of the present invention may be applied to a future type device having a waterproof function.

The porosity of the fiber web 110 according to some embodiments of the present invention is preferably, for example, in a range of 40% to 80%. However, the porosity of the fiber web 110 may vary greatly depending on the occupancy of the conductive circuit patterns 120 or 121 printed on the fiber web 110.

As described above, the wearable flexible printed circuit board according to the embodiment of the present invention has flexibility and air-permeability, has properties of being folded, crumpled and then restored, and is waterproof. Thus, the wearable flexible printed circuit board according to the embodiment of the present invention has excellent physical properties applicable to substrates for wearable devices to be manufactured in the future.

Figure 4:
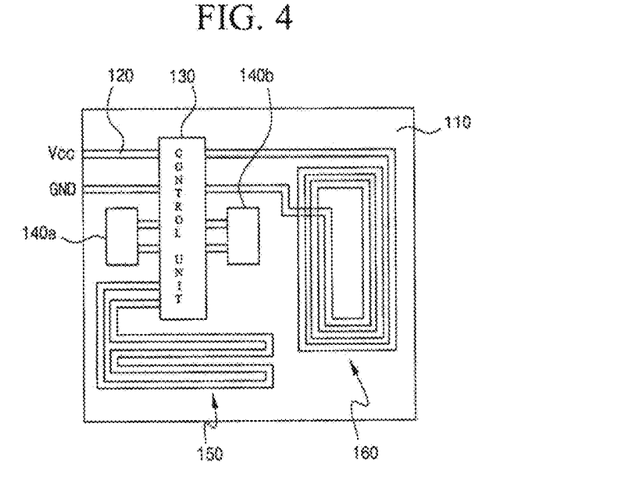
FIG. 4 is a conceptual cross-sectional view illustrating a wearable smart device implemented using a wearable flexible printed circuit board according to an embodiment of the present invention.

FIG. 4 is a conceptual diagram illustrating a wearable smart device implemented using a wearable flexible printed circuit board according to an embodiment of the present invention, in which the fiber web 110 is a flat sheet, and the circuit pattern 120 may be formed by patterning a conductive material on the fiber web 110 in various patterns.

Referring to FIG. 4, a wearable smart device includes: a control unit 130 for performing signal processing, wireless communication, and the like, in which a circuit pattern 120 is formed on a fiber web 110 used as a wearable flexible printed circuit board; a sensor unit 140a including at least one of an electrocardiogram and electromyogram sensor for measuring the heartbeat and respiration of a user so as to be used for telemedicine, a blood glucose/blood pressure sensor, a gas sensor for sensing the neighboring environment, a luminance sensor, and an infra-red sensor, a short range communication module 140b used for short range wireless communication, an antenna pattern 160 used for wireless communication, and a heater pattern 150 for generating heat according to an external environment. Two power terminal terminals Vcc and GND for applying a driving power source Vcc are disposed at one end of the control unit 130.

In this case, various electronic components such as the control unit 130, the sensor unit 140a and the short range communication module 140b are connected to the conductive circuit pattern 120 of the printed circuit board, and the antenna pattern 160 and the heater pattern 150 are formed directly on the fiber web 110 by using a method of printing a conductive paste on the fiber web 110.

Examples of the short range communication technology applied to the short range communication module 140b may include NFC (Near Field Communication), Bluetooth communication, RFID (Radio Frequency Identification) communication, IrDA (infrared data association), UWB (Ultra Wideband) communication, and ZigBee communication.

The wearable smart device may include active electronic components on a wearable flexible printed circuit board as shown in FIG. 4, but may include only passive electronic components without active electronic components.

Figure 14:
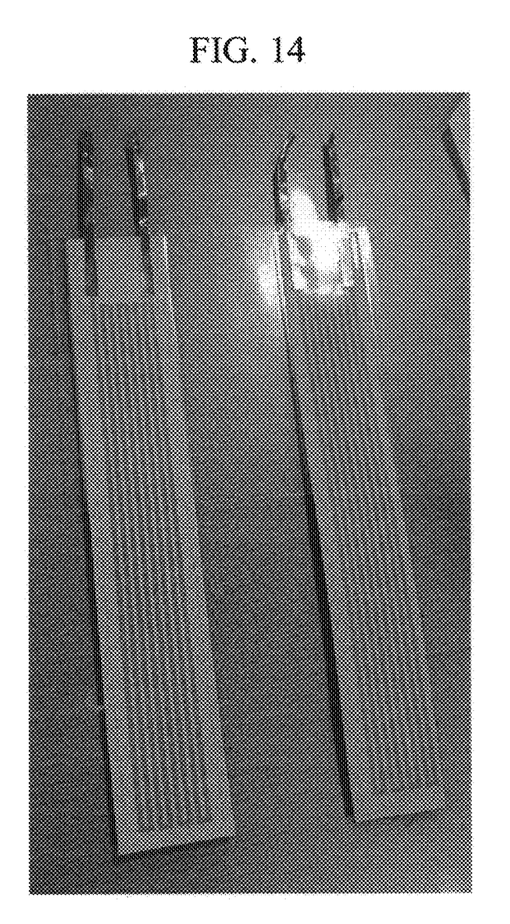
FIG. 14 is a photograph of a sample of a wearable flexible heater implemented by using a wearable flexible printed circuit board according to an embodiment of the invention.

For example, referring to FIG. 14, the heater pattern 150 may be formed by printing a conductive paste on a fiber web 110 by using a screen printing process, and a pair of power terminals may be attached to both ends of the heater pattern 150 by using a conductive adhesive. The thus-implemented wearable flexible heater may be designed in the size and pattern required by the user and may be embedded in the clothes.

Figure 13:
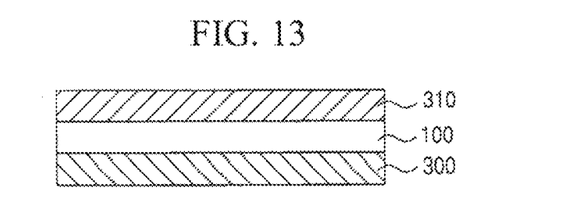
FIG. 13 is a cross-sectional view showing a laminated structure when a wearable flexible printed circuit board according to an embodiment of the invention is applied to a smart garment.

For example, as shown in FIG. 13, a wearable flexible printed circuit board 100 according to an embodiment of the present invention may be inserted between a cloth for lining 300 and a cloth for outsheath 310, so that winter garments may be sewn with a laminated fabric.

In addition, as an example of including only passive electronic components on a printed circuit board without active electronic components, a pair of conductive sensing patterns may be formed spaced apart at intervals by printing the fiber web 110 with a conductive paste to form a predetermined area, and a printed circuit board containing the pair of sensing patterns may be sewn on the inside of a sportswear so as to contact a user's body, to be applied as a biosensor for sensing a user's heart rate.

Further, in addition to the antenna pattern 160 and the heater pattern 150, the circuit pattern 120 may be formed with other types of patterns as needed.

The conductive paste may be an Ag paste or a Cu paste.

The fiber web 110 may have a single-layer structure as shown in FIG. 1, or a three-layer fiber web structure composed of an upper layer, an intermediate layer, and a lower layer. In detail, the fiber web in the intermediate layer may be implemented with a fiber diameter smaller than those of the upper and lower layers, or a web in the form of a non-porous film.

That is, when the conductive paste is printed on the upper layer to form the circuit pattern 120, the conductive paste may penetrate into the pores of the upper layer, wherein relatively small pores defined as small diameter fibers of the intermediate layer of the fibrous web may prevent passage of the conductive paste penetrated from the upper layer and penetration into the lower layer. In addition, when the intermediate layer is a non-porous web, it is possible to completely prevent penetration into the lower layer.

Here, the fiber diameter of the intermediate layer is preferably in a range of 400 nm to 500 nm, and the fiber diameters of the upper layer and the lower layer are preferably more than 500 nm.

As described above, when the printed conductive paste does not pass from one side of the fiber web 110 to the other side thereof, it is preferable that the conductive paste has a thickness of about 20 μm to 100 μm. In this case, it is possible to form the different pattern 120 on the upper and lower surfaces of the fiber web 110.

When the fiber web 110 has a thickness of about 5 μm to 20 μm, the printed conductive paste passes from one side of the fiber web 110 to the other side thereof, and vertical electric conduction is performed between the upper and lower surfaces of the fiber web 110. For example, in the case of the circuit pattern 120 used for a medical patch, it is preferable to use a vertical electric conduction type structure. It is necessary to set the concentration of the paste to be relatively thin and the particle size of the conductive Ag and Cu powder to be large in the conductive paste used for the vertical electric conduction.

A flexible printed circuit board using a conventional polyimide film as a substrate may not realize a vertical electric conduction type substrate.

Figure 5:
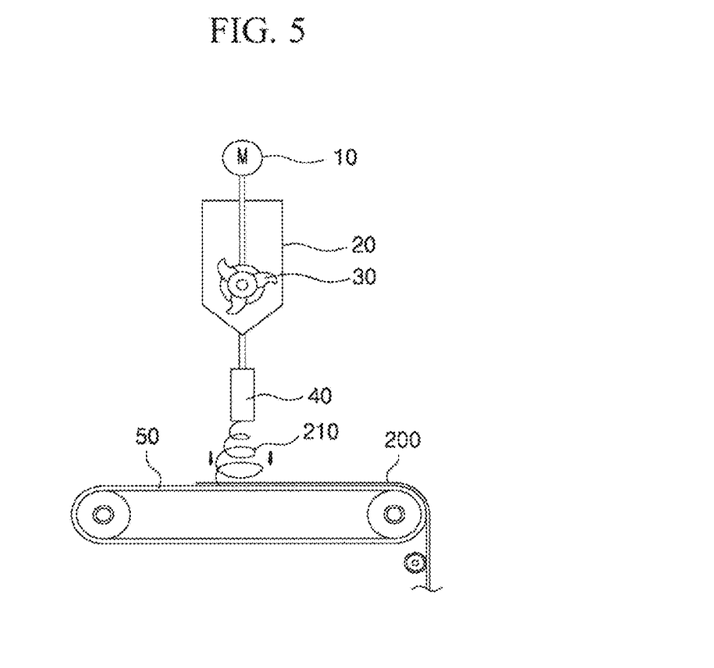
FIG. 5 is a schematic view for explaining an electrospinning apparatus for manufacturing a fiber web applied to a wearable flexible printed circuit board according to an embodiment of the present invention.

FIG. 5 is a schematic view for explaining an electrospinning apparatus for manufacturing a fiber web applied to a wearable flexible printed circuit board according to an embodiment of the present invention.

Referring to FIG. 5, an electrospinning apparatus for manufacturing a wearable flexible printed circuit board according to an embodiment of the present invention is characterized in that a stirring tank 20 for supplying a stirred spinning solution is connected to a spinning nozzle 40, and a grounded collector 50 of a conveyor shape moving at a constant speed is disposed in a lower portion spaced apart from the spinning nozzle 40, in which the spinning nozzle 40 is connected to a high voltage generator (not shown).

Here, the polymer material and the solvent are mixed with a stirrer 30 to prepare a spinning solution. Here, a pre-mixed spinning solution may be used before being put into the electrospinning apparatus without mixing the polymer material and the solvent in the stirring tank 20 with the stirrer 30.

Thereafter, when a high voltage electrostatic force is applied between the collector 50 and the spinning nozzle 40, the spinning solution is spun by the spinning nozzle 40 into the ultrafine fibers 210 to then be emitted to the collector 50. The fibers 210 are accumulated to the collector 50 to form the fiber web 200 of a non-woven fabric.

More specifically, the spinning solution discharged from the spinning nozzle 40 is discharged as the fibers 210 while passing through the spinning nozzle 40 charged by the high voltage generator, and the fibers are sequentially laminated on the grounded collector 50 provided in the form of a conveyor moving at a speed to form the fiber web 110.

Figure 6:
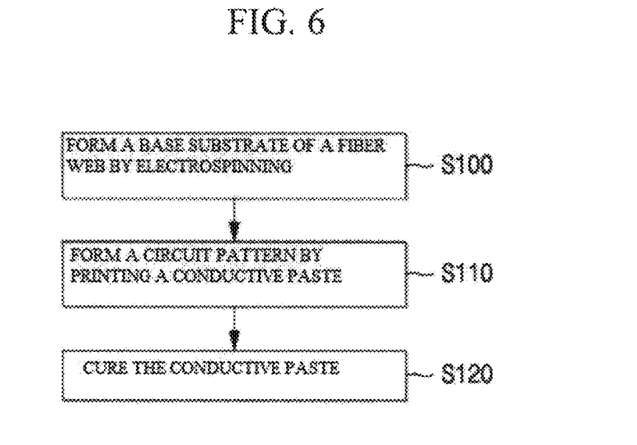
FIG. 6 is a flowchart of a method of manufacturing a wearable flexible printed circuit board according to an embodiment of the present invention.

Referring to FIG. 6, the method of manufacturing a wearable flexible printed circuit board according to an embodiment of the present invention includes the steps of: accumulating and calendering fibers 210 obtained by electrospinning a spinning solution containing a mixture of a polymer and a solvent, to thus form a base substrate made of a fiber web 110 of a desired thickness (S100), printing a conductive paste on the fiber web to form a circuit pattern 120 or 121 (S110), and curing the printed conductive paste (S120).

Here, when the printed conductive paste is an Ag paste, the temperature to be cured is approximately 120° C. to 420° C. Thus, the temperature at which the printed conductive paste is cured may be set in consideration of the melting point of the polymer constituting the fibers.

That is, a single polymer or a mixed polymer capable of withstanding the curing temperature of the printed conductive paste may be applied. For example, PU (polyurethane) may be applied when curing at a low temperature of 200° C. or less, and polyacrylonitrile (PAN) and PES (polyether sulfone) may be applied when curing at a high temperature in excess of 200° C.

Figure 15:
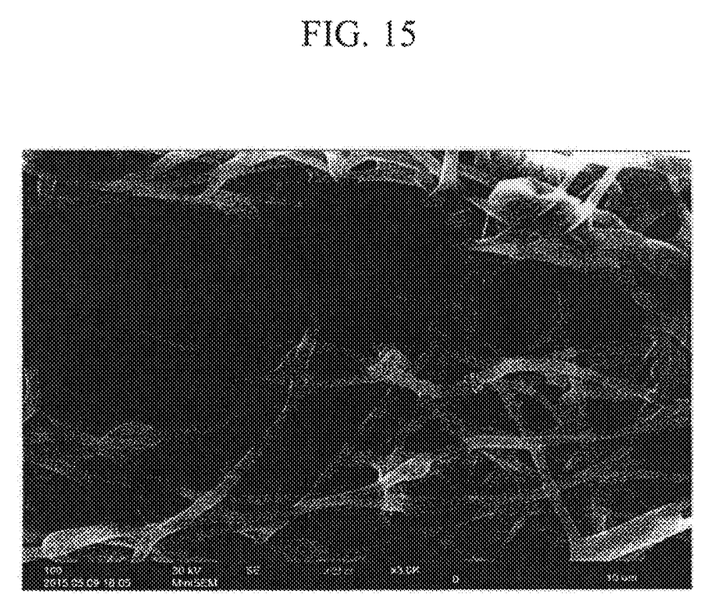
FIG. 15 is a photograph showing a SEM image in which a wearable flexible printed circuit board according to an embodiment of the invention is magnified.
Figure 16:
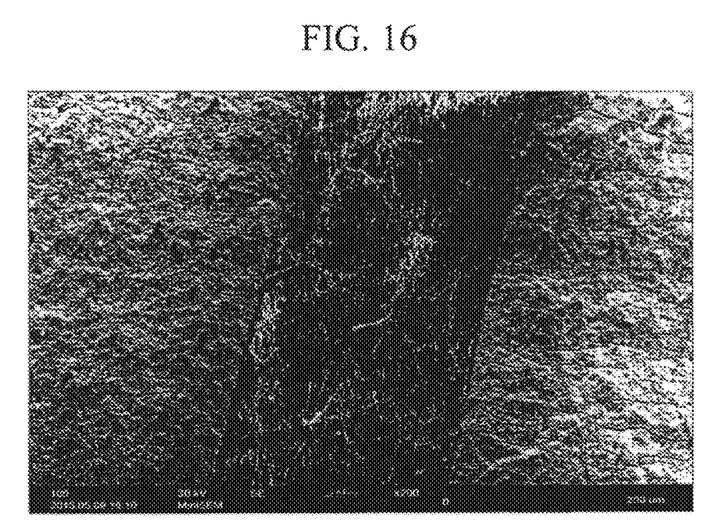
FIG. 16 is a SEM image obtained by enlarging and photographing a portion printed with a conductive circuit pattern on a wearable flexible printed circuit board according to an embodiment of the invention.
Figure 17:
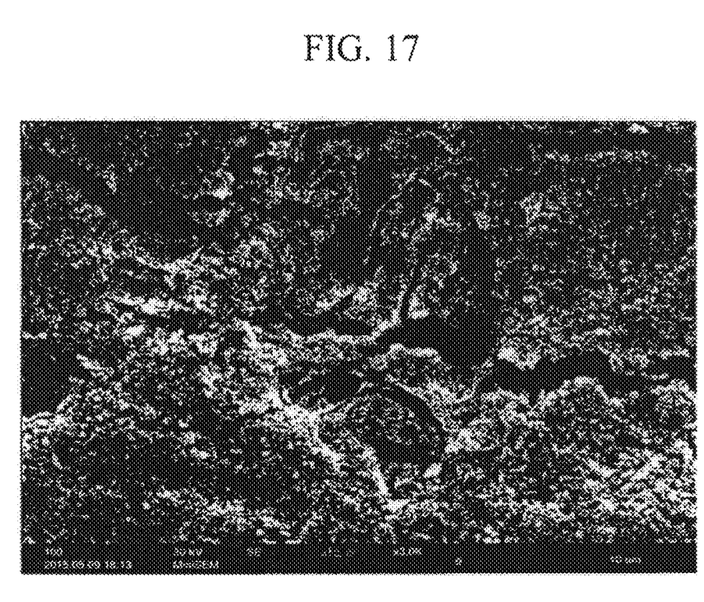
FIG. 17 is a SEM image obtained by enlarging and photographing a conductive circuit pattern printed on a wearable flexible printed circuit board according to an embodiment of the invention.

FIG. 15 shows a SEM (Scanning Electron Microscope) image obtained by enlarging and photographing a fiber web applied to a wearable flexible printed circuit board according to an embodiment of the present invention, at a magnification of 3000 times. FIG. 16 shows a SEM image obtained by enlarging and photographing a portion where a circuit pattern obtained by screen printing an Ag paste on a fiber web and sintering at 120° C. is arranged at either side of the fiber web, at a magnification of 200 times. FIG. 17 shows a SEM image obtained by enlarging and photographing a portion of the circuit pattern at a magnification of 3000 times.

Figure 7A:
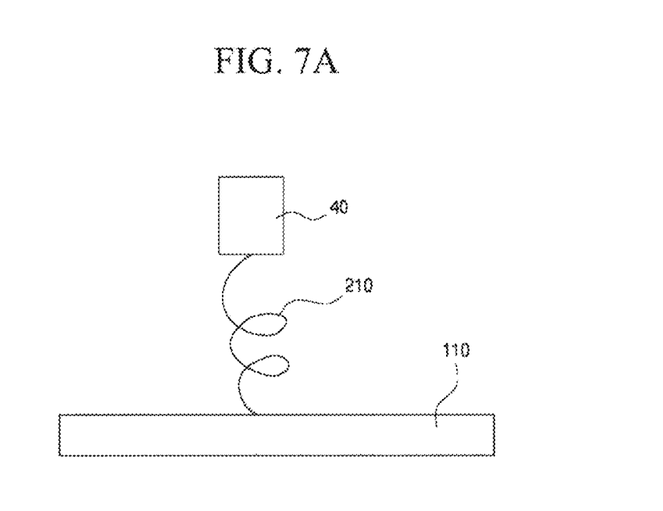
FIGS. 7A and 7B are conceptual cross-sectional views illustrating a method of manufacturing a wearable flexible printed circuit board according to an embodiment of the present invention.

Referring to FIGS. 5 and 7A showing a spinning apparatus, the spinning solution discharged from the spinning nozzle 40 is discharged to the fibers 210 while passing through the spinning nozzle 40 charged by the high voltage generator, and the fibers 210 are sequentially laminated on top of the grounded collector 50 of the conveyor shape moving at a constant speed, to thereby form the fiber web 110 of step S100.

Figure 12:
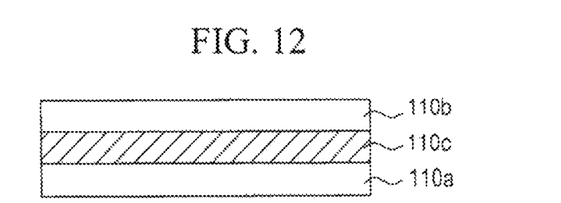
FIG. 12 is a cross-sectional view showing a base substrate that may be applied to a wearable flexible printed circuit board according to an embodiment of the present invention.

When the base substrate constituting the wearable flexible printed circuit board is insufficient in strength only by a single layer of the fiber web 110, a nonwoven fabric may be used as a strength reinforcing support 110c as shown in FIG. 12, and first and second fiber webs 110a and 110b may be laminated on one or both sides of the strength reinforcing support 110c, to form a multilayer structure.

Figure 7B:
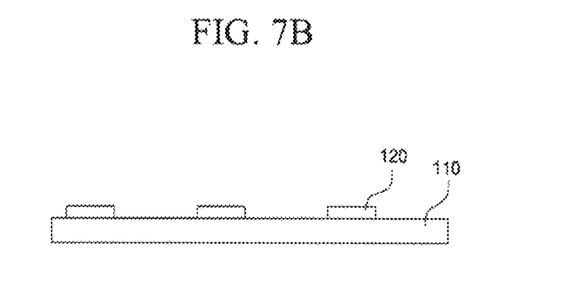

As shown in FIG. 7B, the conductive paste is printed on the fiber web 110 to form the circuit pattern 120, in step S110.

When this process is performed, the circuit pattern 120 is printed on the fiber web 110. Here, as shown in FIG. 8, the circuit pattern 121 may be formed by filling the fibers 210 and the pores 211 of the fiber web 110 with a conductive paste. As shown in FIG. 9, the circuit pattern 121 may be formed only on the fibers 210.

Meanwhile, in some embodiments of the present invention, the flexibility of the wearable flexible printed circuit board may be maximized by applying a fiber web having substantial corrugated fibers.

Figure 10:
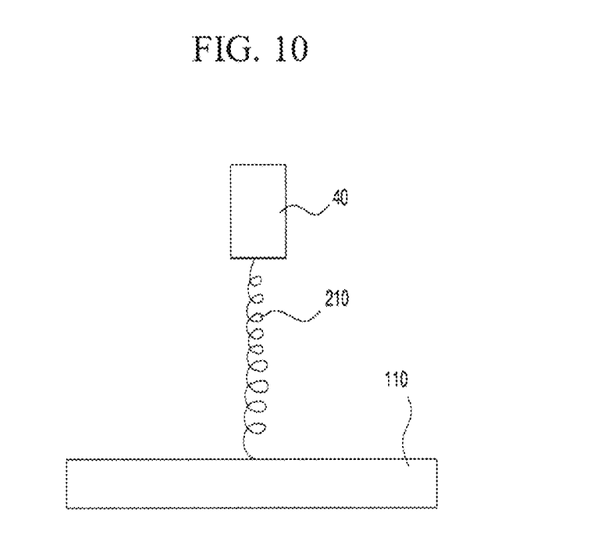
FIG. 10 is a view for explaining a method of forming a fiber web having corrugated fibers applied to a wearable flexible printed circuit board according to an embodiment of the present invention.
Figure 11:
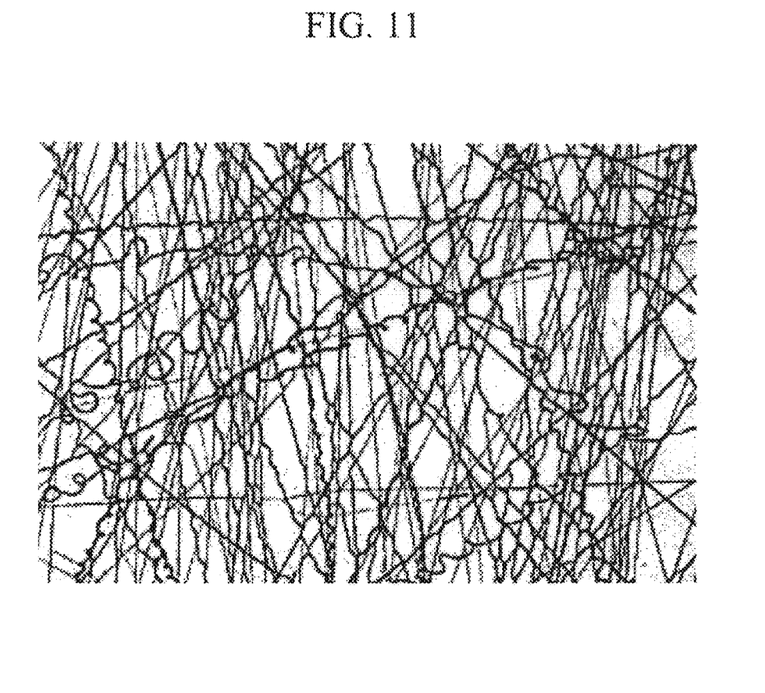
FIG. 11 is a SEM image showing an enlarged photograph of a fiber web having corrugated fibers applied to a wearable flexible printed circuit board according to an embodiment of the present invention.

That is, as shown in FIG. 10, when the radius of rotation of the fibers 210 emitted from the spinning nozzle 40 is reduced by electrospinning, substantially corrugated fibers as shown in the SEM photograph of FIG. 11 are accumulated to form a fiber web. Here, if the radius of rotation of the fiber 210 discharged from the spinning nozzle 40 is large, the fibers 210 having a linear shape are accumulated.

The radius of rotation of the fibers 210 emitted from the spinning nozzle 40 is involved with the humidity environment of electrospinning and the polymer concentration in the spinning solution.

First, when electrospinning in a high-humidity environment, the volatility of the solvent in the fibers 210 discharged from the spinning nozzle 40 is accelerated, the diameter of the fibers 210 becomes thick, and the fibers 210 fall down with a small radius of rotation to then be accumulated. As a result, the fiber web 110 is made by accumulating the corrugated fibers 210. In some embodiments of the present invention, the high humidity environment may be set to have a humidity of 60% to 80%.

In other words, when the concentration of the solvent in the fibers 210 discharged from the spinning nozzle 40 is lowered, the corrugated fibers 210 are accumulated.

On the contrary, under a low humidity environment, the volatility of the solvent in the fibers 210 discharged from the spinning nozzle 40 is slowed down, the diameters of the fibers 210 becomes smaller, and the fibers fall and accumulate with a large turning radius. Therefore, the fibers 210 of approximately linear shape are accumulated to form the fiber web 110. Here, the low humidity environment may be set to an environment having a humidity of 60% or less, preferably a humidity of 45% or more and less than 60%.

Further, when the concentration of the polymer in the spinning solution is high, the concentration of the solvent contained in the fibers 210 discharged from the spinning nozzle 40 is low to produce the corrugated fiber 210. Conversely, when the polymer concentration is low, the concentration of the solvent contained in the fibers 210 increases to produce straight fibers 210.

While the present invention has been particularly shown and described with reference to exemplary embodiments thereof, by way of illustration and example only, it is clearly understood that the present invention is not to be construed as limiting the present invention, and various changes and modifications may be made by those skilled in the art within the protective scope of the invention without departing off the spirit of the present invention.

INDUSTRIAL APPLICABILITY

The present invention is applied to a wearable flexible printed circuit board that may be applied to a wearable smart device by forming a circuit pattern on a fiber web formed by accumulating fibers, thereby improving flexibility, restoring property, waterproofness, and air-permeability.

What is claimed is:

1. A wearable flexible printed circuit board comprising:
   a base substrate made of a fiber web that is formed by accumulating spun fibers made of a fiber-forming polymer material and having a diameter of 3 μm or less; and
   a conductive circuit pattern formed on the base substrate, wherein the fiber web has a plurality of pores; and
   wherein the circuit pattern is formed on only fibers of the fiber web.

2. The wearable flexible printed circuit board of claim 1, wherein the circuit pattern is formed by filling a conductive paste into the fibers and the pores of the fiber web.

3. The wearable flexible printed circuit board of claim 1, wherein the fiber web is formed by accumulating fibers obtained by electrospinning a spinning solution containing a mixture of a polymer material and a solvent.

4. The wearable flexible printed circuit board of claim 1, wherein the base substrate has a thickness of 20 μm to 100 μm and wherein, when the circuit pattern is formed on either of upper and lower sides of the base substrate, respectively, the circuit patterns formed on the upper and lower sides are not electrically conducted with each other.

5. The wearable flexible printed circuit board of claim 1, wherein the thickness of the base substrate is in a range of 5 μm to 20 μm, and the circuit patterns formed on the base substrate are vertically electrically conducted.

6. The wearable flexible printed circuit board of claim 1, wherein the circuit pattern is formed by a conductive paste printed on the fiber web.

7. The wearable flexible printed circuit board of claim 1, wherein the base substrate further comprises:
   a strength reinforcing support; and
   the fiber web laminated on one side or both sides of the support.

8. The wearable flexible printed circuit board of claim 1, wherein the fiber web is a three-layer fiber web structure composed of an upper layer, an intermediate layer and a lower layer, and the intermediate layer of the fiber web is thinner than the upper or lower layer in diameter, or a non-porous web.

9. The wearable flexible printed circuit board of claim 1, wherein the fibrous web has a porosity in a range of 40% to 80%.

10. A wearable smart device comprising:
    a wearable flexible printed circuit board according to claim 1; and
    at least one electronic component mounted on the wearable flexible printed circuit board.

11. The wearable smart device of claim 10, wherein the electronic component comprises: a sensor unit including at least one of a biosensor for detecting a user's physical condition and an environmental sensor for sensing a surrounding environment; a short range communication module used for short range wireless communication; an antenna pattern used for wireless communication; and a control unit for performing a signal processing function.

12. The wearable smart device of claim 11, wherein the electronic component further comprises: a heater pattern for generating heat according to an external environment.

13. The wearable smart device of claim 12, wherein the antenna pattern and the heater pattern are directly formed on the printed circuit board using a conductive paste.

14. The wearable smart device of claim 10, wherein the electronic component is one of a bio sensor and a heater pattern for detecting a user's body condition.

15. The wearable smart device of claim 10, wherein the wearable smart device is embedded between a cloth for lining and a cloth for outsheath, or laminated inside the cloth for lining.

16. A wearable flexible printed circuit board comprising:
    a base substrate made of a fiber web that is formed by accumulating spun fibers made of a fiber-forming polymer material and having a diameter of 3 μm or less; and
    a conductive circuit pattern formed on the base substrate, wherein the thickness of the base substrate is in a range of 5 μm to 20 μm, and the circuit patterns formed on the base substrate are vertically electrically conducted.

17. A wearable flexible printed circuit board comprising:
    a base substrate made of a fiber web that is formed by accumulating spun fibers made of a fiber-forming polymer material and having a diameter of 3 μm or less; and
    a conductive circuit pattern formed on the base substrate, wherein the fiber web is a three-layer fiber web structure composed of an upper layer, an intermediate layer and a lower layer, and the intermediate layer of the fiber web is thinner than the upper or lower layer in diameter, or a non-porous web.

18. A wearable flexible printed circuit board comprising:
    a base substrate made of a fiber web that is formed by accumulating spun fibers made of a fiber-forming polymer material and having a diameter of 3 μm or less; and
    a conductive circuit pattern formed on the base substrate, wherein the fiber web is in a non-porous form.

* * * * *